US010191194B2

(12) United States Patent
Kruschwitz et al.

(10) Patent No.: US 10,191,194 B2
(45) Date of Patent: Jan. 29, 2019

(54) SPECTRAL TARGET FOR MACROSCOPIC AND MICROSCOPIC REFLECTANCE IMAGING

(71) Applicants: Jennifer D. T. Kruschwitz, Rochester, NY (US); Roy S. Berns, Pittsford, NY (US)

(72) Inventors: Jennifer D. T. Kruschwitz, Rochester, NY (US); Roy S. Berns, Pittsford, NY (US)

(73) Assignee: Rochester Institute of Technology, Rochester, NY (US)

( * ) Notice: Subject to any disclaimer, the term of this patent is extended or adjusted under 35 U.S.C. 154(b) by 177 days.

(21) Appl. No.: 14/933,839

(22) Filed: Nov. 5, 2015

(65) Prior Publication Data

US 2016/0124130 A1    May 5, 2016

Related U.S. Application Data

(60) Provisional application No. 62/075,389, filed on Nov. 5, 2014.

(51) Int. Cl.
*G01J 3/44*    (2006.01)
*G02B 5/28*    (2006.01)
(Continued)

(52) U.S. Cl.
CPC ................ *G02B 5/28* (2013.01); *G01J 3/28* (2013.01); *G01J 3/52* (2013.01); *G01J 3/524* (2013.01);
(Continued)

(58) Field of Classification Search
CPC .... G01J 3/28; G01J 3/52; G01J 3/524; G01N 21/25; G01N 21/278; G02B 5/26; G02B 5/28; G02B 3/0006; H04N 17/002
(Continued)

(56) References Cited

U.S. PATENT DOCUMENTS 5,825,483 A * 10/1998 Michael ............... G01B 11/002
                                                   356/237.1
5,838,435 A * 11/1998 Sandison ................. G01J 3/28
                                                   250/252.1
(Continued)

OTHER PUBLICATIONS

McCamy, C.S., Marcus, H., Davidson, J.G., A Color-Rendition Chart, Journal of Applied Photographic Engineering, vol. 2, No. 3, Summer 1976, pp. 95-99.

*Primary Examiner* — Hoa Pham
(74) *Attorney, Agent, or Firm* — Bond, Schoeneck & King, PLLC; Joseph Noto

(57) ABSTRACT

A spectrally selective (e.g., color) target has been designed and fabricated for reflectance micro- and/or macro-imaging that utilizes microlens arrays and color mirrors. The color mirrors are optical interference coatings. The microlenses are designed and fabricated such that the light reflected from the color mirror is incident onto the detector. This system of microlenses and color mirrors allows the user to image different colored specular highlights. An infinite number of spectral reflectance profiles can be created with these color targets and used for spectral and colorimetric imaging applications. The targets are not limited to the visible region; they can also be designed to work in the ultraviolet and infrared wavelength regions.

9 Claims, 9 Drawing Sheets

(51) Int. Cl.
*H04N 17/00* (2006.01)
*G01J 3/52* (2006.01)
*G01N 21/25* (2006.01)
*G01N 21/27* (2006.01)
*G01J 3/28* (2006.01)
*G02B 3/00* (2006.01)

(52) U.S. Cl.
CPC ........... *G01N 21/25* (2013.01); *G01N 21/278* (2013.01); *H04N 17/002* (2013.01); *G02B 3/0006* (2013.01)

(58) Field of Classification Search
USPC .......... 356/300–301, 319, 326, 243.1–243.8, 356/445–448; 359/642, 14, 619–625, 359/572, 25
See application file for complete search history.

(56) References Cited

U.S. PATENT DOCUMENTS

| | | | | |
|---|---|---|---|---|
| 5,930,418 A * | 7/1999 | Chang | ................... | G02B 6/2746 385/11 |
| 6,471,916 B1 * | 10/2002 | Noblett | ................ | C12Q 1/6837 250/252.1 |
| 7,968,839 B2 * | 6/2011 | Merenda | ................ | G21K 1/006 250/251 |
| 8,519,315 B2 * | 8/2013 | Griffith | ................ | G01J 1/4257 250/201.9 |
| 8,624,174 B2 * | 1/2014 | Griffith | ................ | G01J 1/4257 250/214.1 |
| 2010/0103527 A1 * | 4/2010 | Endle | ........................ | B44F 7/00 359/620 |
| 2013/0188035 A1 | 7/2013 | Goodwin | | |
| 2014/0055592 A1 | 2/2014 | Wei et al. | | |

* cited by examiner

SPECTRAL TARGET FOR MACROSCOPIC AND MICROSCOPIC REFLECTANCE IMAGING

CROSS REFERENCE

This application claims the benefit of the filing date of U.S. Provisional Patent Application Ser. No. 62/075,389, filed Nov. 5, 2014, which is hereby incorporated by reference in its entirety.

FIELD

The present invention relates to a spectral target for macroscopic and microscopic reflectance imaging, and in particular, to a spectral target utilizing a mirror-like substrate containing one or more microlenses having an opaque multi-layer coating where the coating is spectrally selective, producing, e.g., one or more color mirrors.

BACKGROUND

In macroscopic imaging, painted color targets are often used to calibrate and characterize cameras and scanners. For image capture under magnification, such as with a loupe or microscope, determining the color ground truth becomes more challenging because such targets are spatially non-uniform (rough) under magnification. An interference coating, color mirror target is more advantageous to use under magnification compared to a traditional painted target because mirrors are smooth under magnification. Photolithographic techniques can be used to create small and very advanced color mirror arrays so that many colors can be captured in a single image, no matter the magnification. The small arrays will have a similar reflected spectral performance when compared to a larger sample from the same fabrication cycle. Sedgewick, "Improving Color Consistency, Color Integrity and Consequent Speed in Reading Slides," DataColor, 2014, 28 Apr. 2014, which is hereby incorporated by reference in its entirety. Photolithography is not compatible with paint. Paint consists of many sized particles that do not create homogeneous color under magnification and there can be shadowing or contamination that changes the color in localized regions. Color mirrors are fabricated under vacuum on smooth, specular surfaces reducing the probability of particulate contamination. The mirror's specular surface allows one to image their colors with only a small fraction of the light necessary compared to painted samples, allowing for shorter exposure times. Paint is susceptible to environmental conditions and will fade over time; color mirrors do not fade. Interference coating designs can create spectral reflectance profiles of any shape imaginable for not only the visible wavelength region, but also the ultraviolet and infrared regions, allowing one target to be used with a variety of camera sensors. They can also be used to create highly chromatic color mirrors. This ability expands the color gamut of a target, which is useful when imaging objects, such as bird feathers or butterfly wings. This expansion is an additional advantage compared with painted samples. There are many coatings incorporating color mirrors and metals such as automotive finishes and nail polish where the expanded target is more appropriate for instrument calibration and verification. Lastly, interference coatings can be used to create an ideal training target for spectral reflectance reconstruction in multispectral imaging applications reducing the sample number significantly from those using paint. N. Tsumura, H. Sato, T. Hasegawa, H. Haneishi, Y. Miyaki, "Limitation of color samples for spectral estimation from sensor responses in fine art painting," Optical Review, 6, pp. 57-61 (1999) which is hereby incorporated by reference in its entirety. One issue with these color mirrors is their spectral sensitivity to Increasing incidence angle. The spectral reflectance will shift to lower wavelengths at higher Incidence angles. Fortunately, there are design techniques that can be utilized to minimize the Angular sensitivities of interference coatings. J. D. T. Kruschwitz, "designing non-polarized High reflecting coatings within immersed high-index media," in optical interference coatings, Page tub3; optical society of america (2001); j. D. T. Kruschwitz, r. S. Berns, "non-Polarizing color mirrors on a high reflecting metal base," appl. Opt. 53, no. 16, pp. 3448-3453 (2014), which is hereby incorporated by reference in its entirety.

For transmission microscopy, an array of colored gels or interference bandpass filters has been used successfully as color targets. Sedgewick, "Improving Color Consistency, Color Integrity and Consequent Speed in Reading Slides," DataColor, 2014, 28 Apr. 2014; Y. Yagi, "Color standardization and optimization in whole slide imaging," Diagn Pathol, 6, Suppl 1:S15 (2011), which is hereby incorporated by reference in its entirety. These filters are not as convenient to use in an off-axis reflection system because they are flat and specular, and these microscopy systems are typically used to image diffuse reflected color. Light sources that are placed at 45° incident to a flat, specular sample will have their light reflect off the surface at the opposite 45° never entering the microscope lens.

SUMMARY

An aspect of the present invention includes a spectral target for determining the spectral reflectance factor and/or colorimetric coordinates of a sample including a mirror-like substrate containing a microstructure on the surface of the substrate and having an opaque multi-layer spectrally selective coating.

Another aspect of the present invention includes a system for determining the spectral reflectance factor and/or colorimetric coordinates of a sample including a spectral target including a substrate, a microstructure including a microlens on the surface of the substrate, and a spectrally selective mirror-like coating on the surface of the microstructure; a source of electromagnetic radiation; and a micro- or macro-imaging device, wherein the spectral target is adapted by designing the shape of the microlens to reflect electromagnetic radiation from the source into the micro- or macro-imaging device.

Another aspect of the present invention includes to a method for determining the spectral reflectance factor and/or colorimetric coordinates of a sample including providing a spectral target; calibrating a camera by reflecting a source of electromagnetic radiation off the spectral target to establish a spectral reflectance and/or colorimetric baseline; reflecting the electromagnetic radiation off a sample into a micro- or macro-imaging device; and determining the spectral reflectance and/or color of at least a portion of the sample as a function of wavelength of the electromagnetic radiation using the spectral reflectance factor and/or colorimetric baseline of the spectral target, wherein the spectral reflectance factor and/or colorimetric baseline determined regardless of an angle of incidence of the source of electromagnetic radiation.

These and other aspects of the present invention will become apparent upon a review of the following detailed description and the claims appended thereto.

DETAILED DESCRIPTION

Figure 1:
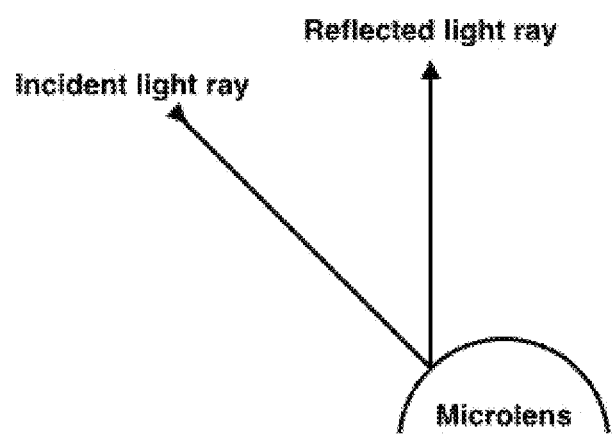
FIG. 1 shows the result of an incident light reflecting off of a convex lens.

The present invention relates to a spectral target, system, and a method for calibrating and verifying the spectral reflectance of a sample using macroscopic or microscopic reflectance imaging. The spectral target utilizes a mirror-like substrate containing microstructures, e.g., microlenses, with an opaque multi-layer coating where the coating is spectrally selective.

A spectral target in accordance with the present invention includes a substrate with a mirror-like surface, having microstructure features and interference coatings. For example, the surface can have an optical quality finish, such that the predominant feature of incident light reflected from the surface is specular, and not diffuse. A mirror-like surface can be provided on the substrate by a single opaque metal film applied to the substrate surface. This is commonly accomplished by evaporating aluminum on float glass in a vacuum. Mirror-like surfaces reflect incident light at the opposite angle to the incident angle. The mirror-like surface can be coated with a multi-layer thin film that changes the amount of mirror-like reflection as a function of wavelength, sometimes referred to as a color mirror when the wavelength selectivity is within the visible spectrum. This spectral target is used to calibrate and verify the scale of spectral reflectance factor and colorimetric coordinates by providing reference values obtained using non-imaging spectral devices including spectrophotometers and spectroradiometers.

The surface of the substrate has microstructure features. These features can be formed from a structured surface or can be composed of a single microstructure or multiple microstructures attached to the substrate surface. For example, the structured surface can be a collection of microstructures, such as microlenses or other micron-sized optical elements, having structures of known physical profile. The substrate surface can include a single feature or an array of features. The shape of the microstructure features includes, e.g., spheres, cones, pyramids, concave or convex miniature lenses, edges, ridges, slopes, and the like. Microstructures in accordance with the present invention include microlenses, retro-reflectors, pyramid, moth-eye, Fresnel structures, and the like. This size of the features on the surface are within the range of reflected light, not diffracted light, and remain greater than about 1.22λ (the diffraction limit). The size of an individual optical feature is less than about 2500 times the wavelength of incident light. The substrate surface can be composed of stand-alone, individual optical features or multiple optical features arranged in an array.

Each feature has a mirror-like finish and is coated with a multilayer thin film such that the reflected light can have a specific spectral reflectance profile. The multilayer thin film can be all dielectric or a combination of metal-dielectric layers. Multiple interference coatings can be applied to the surface of the substrate to provide multiple spectral selectivity profiles in multiple locations. For example, a single color mirror can have multiple interference coatings that reflect multiple colors. When the incident light rays on the substrate are within the visible wavelength region, this spectral reflectance profile is described as a color mirror. The functionality of the reflectance spectral profile is not limited to the visible wavelength region, and the multilayer thin film can be designed to reflect a specific spectral profile for the ultraviolet through the far infrared wavelength regions. The combination of the substrate surface features, mirror-like surface and the multilayer thin film creates a specular, spectral reflectance target that, for example, can be imaged onto a detector or into an eyepiece. In an embodiment, when illuminated, the color reflected in the specular highlight is imaged and can be used to either color or spectrally calibrate a microscope imaging system using linear transformations between input camera signals and output spectral reflectance factor or colorimetric coordinates such as tristimulus values. For example, Ribés, A., & Schmitt, F. (2008), Linear Inverse Problems In Imaging, *IEEE Signal Processing Magazine*, 25(4), 84-99, which is hereby incorporated by reference in its entirety. The surface feature has the ability to direct bundles of incident light rays via reflectance and image them to a detector or eyepiece in a manner such that the incident light rays can be predicted by first-order geometrical optics calculations. The spectral target can produce, for example, a microscope image pattern such as that illustrated in FIG. 3 wherein a location in the pattern can be assigned a certain wavelength or range of wavelengths, e.g., a color, which then can be used to calibrate the imaging system and for other imaged materials, assign a spectral reflectance factor or colorimetric coordinates. In an embodiment, a microstructure is selected, such as a sphere or cylinder, such that some portion of the reflected light reaches the detector or into the microscope regardless of the angle of incidence of the source. The detected reflected light results in an image pattern that can be generated regardless of the angle of incidence of the incoming light. A location in the patterned image can be used to determine the color of a sample by subjecting the sample to a relatively similar angle of incidence of the source light.

An embodiment includes an array of color mirrors deposited on a substrate having a single opaque metal film surface where the microstructures are microlenses having surfaces with differing lens slopes. The color mirrors all produce their individual color spectral highlights, therefore allowing a single image to be used for color and/or spectral calibration. Other forms of the substrate include a series of mirrors imaged sequentially, providing collective images that can be used for calibration and verification.

A system for determining the spectral reflectance of a sample in accordance with the present invention includes a spectral target having a substrate with a mirror-like surface, microstructure features and interference coatings; a light source, either off-axis or on-axis; and a microscope or camera, wherein the mirror-like spectral target is adapted to reflect the off-axis or on-axis light into the microscope or camera. The functionality of the reflectance spectral profile is not limited to the visible wavelength region, and the multilayer thin film can be designed to reflect a specific spectral profile for the ultraviolet through the far infrared wavelength regions.

Figure 3:
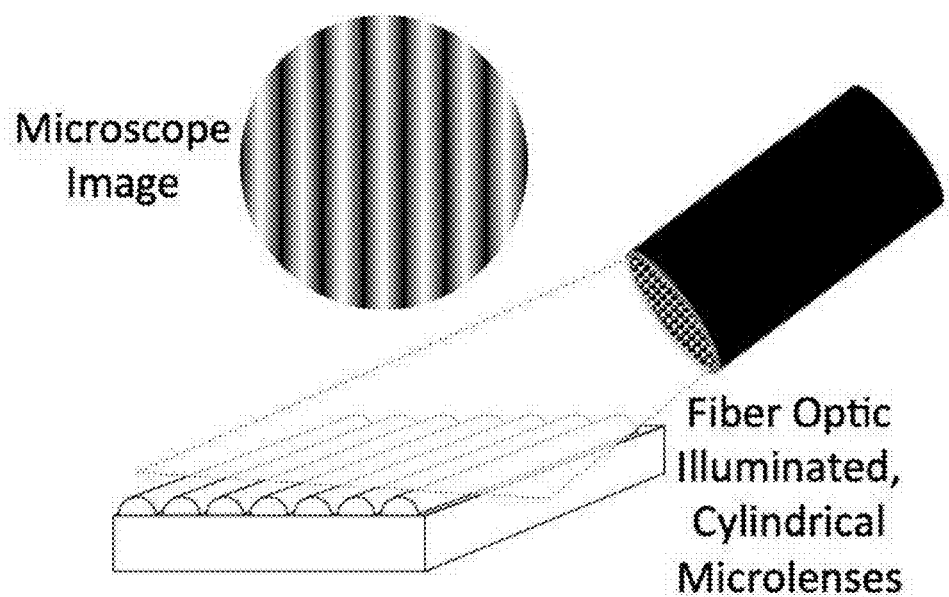
FIG. 3 illustrates a light source illuminating a spectral target containing a microlens and a microscope reflected image off the spectral target, in accordance with an embodiment of the present disclosure.

A method for determining the spectral reflectance of a sample in accordance with the present invention includes providing a mirror-like spectral target or targets. For the single target, identifiable gridded regions each have the same interference coating. For multiple targets, each target has the same interference coating. An imaging system is also provided having off-axis or on-axis illumination and a microscope, or magnifier and detector, or a camera having both a lens and sensor. The sensor can have one or more channels, each with a unique spectral sensitivity. Each coating has reference spectral reflectance and/or colorimetric coordinates, obtained by measuring a larger sample from the same fabrication sample using a reference spectrophotometer or spectroradiometer. An image or images of each color mirror are collected and signals recorded of each target area with the same interference coating. For each color mirror, the microlens produces a periodic pattern as shown in FIG. 3. Any consistent location can be used to record camera signals. The locations can be defined based on the geometry of the microlense pattern and magnification. Another approach is to use a thresholding technique where a small range of signal values identify the locations, based on imaging a spectrally nonselective color mirror. Commonly, a range near the maximum signal value is used; for the microscope image shown in FIG. 3, the locations would correspond to the white stripes, shown in FIG. 4 A transformation is derived that relates these averaged signals for each interference coating and for each camera channel to spectral reflectance factor or colorimetric coordinates using the reference data. This method calibrates the imaging system to the scale of spectral reflectance factor and/or colorimetry. This transformation is used in subsequent imaging to produce images that record the scale of spectral reflectance factor and/or colorimetry.

The spectral reflectance signatures can be designed for electromagnetic radiation outside the visible wavelength region. The mirrors could be designed with specific reflectance profiles, for example, in the infrared as well. This would create a target that can be used for imaging systems that have sensors with spectral sensitivities beyond the visible spectrum.

The present invention can be useful as a color target. A color target can be used for spectral and/or color calibration of images recorded through a microscope or camera system. The target could be used in reflectance, and imaged such that CIE colorimetric coordinates and spectral reflectance profiles can be determined for a plurality of illumination and reflectance conditions. A transformation matrix can be created from the imaged data connecting the camera sensitivities to CIE colorimetric coordinates and spectral reflectance factor profiles. This transformation matrix data can be used to calibrate the color of images of unknown specimens and faithfully reproduce that calibrated color on an array of display and printing devices.

Another major use would be in the medical imaging field, specifically in the areas of Dermatology and Ophthalmology. There is currently no way to color calibrate digital images taken under magnification of human skin or of the human retina. One major use in these fields would be for color calibration of multiple imaging systems used for clinical trials of drugs. Having one color target used by all clinicians allows direct comparison of images from before and after drug use. Without a way to compare the color of all images directly, there is no logical way to know if the drugs used are working in a positive manner.

A further major use of such a color target would be in the area of MEMS device fabrication. The color target would allow magnified images of areas of the MEMS device to be analyzed in terms of reflected color post-process, revealing accurate fabrication of micron-sized attributes. This method would work extremely well for visual inspection of new camera sensors, for example. Currently, a separate, large witness sample is used to determine accurate manufacture of the device. With a calibrated imaging system, a single image can be used to determine if the actual device meets all of the known fabrication specifications.

The following are potential uses: used to calibrate cameras for reflection microscope manufacturers; used by pathologists to calibrate their own microscope cameras; used by dermatologists to calibrate their cameras/displays; used by museums to calibrate their microscope cameras/displays; and used by MEMS manufacturers to calibrate their imaging systems based on fabrication needs.

Another use for this invention is to be able to spectral and/or color calibrate reflectance microscope imaging systems or imaging systems that capture reflected light under magnification. Compound microscopes are used in the art world for museum archiving of pigments used in paintings, pottery, and textiles created by Master artists. There is currently no reliable way to color calibrate microscopes used in the discipline. Data collected from magnified images of paintings would reveal the spectral reflectance profiles of pigments used and would allow the museum professionals to better color match areas that are being repaired or cleaned.

Another use for this invention is to be able to spectral and/or color calibrate imaging systems that are used to image objects having coatings containing interference pigments, metallic pigments, and other so-called effect pigments.

Figure 2:
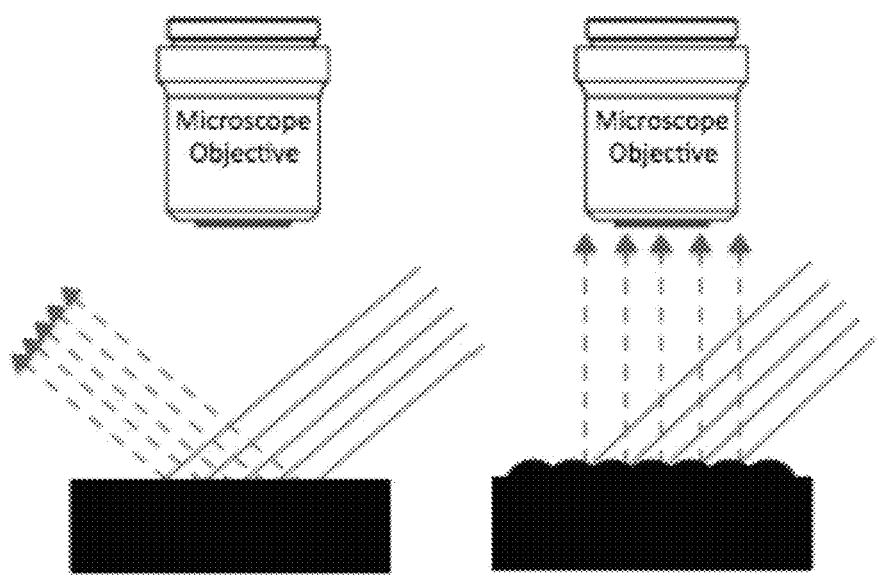
FIG. 2 shows a comparison of specular light being reflected off a comparative flat surface (left image) and in accordance with an embodiment of the present disclosure, specular light reflected off a microstructure surface (right image) up into the microscope when the incident plus reflected angles total 45° when the spectral target contains convex lenses.

An important factor to capturing specular reflected light is to create a surface structure similar to a convex mirror as shown in FIG. 1 that will reflect the incident light up into the microscope. A suitable configuration is shown in FIG. 2. In FIG. 2, convex microlenses reflect the specular light up into the microscope and are imaged as a specular highlight off of the individual microlenses. Specular light can be reflected up into the microscope if the incident plus reflected angles total 45°. This can happen if the sample contains convex lenses (FIG. 2, right).

Some microscopes use on-axis illumination. In this case, the incident and reflected light are at identical angles. Using a concave microlens, the specular light can be reflected up into the microscope.

The present invention combines the optical properties of lenses and interference coatings into a spectral target, system, and method such that spectrally selective specular reflections can be aimed towards an imaging detector for any combination of incidence and collection angles. Once the angles are defined, a microlens is designed to reflect specular light towards the imaging detector.

Spectrally selective optical radiation achieved using principles of optical interference produce colors with much greater chromatic intensity than using conventional pigments and dyes that produce color only by absorption and scattering. Multi-layer coatings can be readily designed and fabricated that tune the spectral selectivity enabling optimal calibration and verification targets when imaging in the ultraviolet, visible, and infrared regions of the electromagnetic spectrum.

In photography, a specular highlight can give an indication of the gloss associated with an object. It can also indicate the direction and color of the incident light source. In many imaging techniques it may be required to clip the highlight to increase the contrast of the image. Specular highlights from shiny color mirrors are not solely the color of the incident illumination. It is the combination of the spectral power distribution of the source and the spectral reflection of the color mirror. The highlights created on the surface of these color mirrors are not white unless the color of the mirror is silver; they represent the color of the light source and the spectral reflectance of the surface of the color mirror combined. Optical interference coatings give more color combinations than can be produced by any other metallic coloring process, and the reflectance profiles can be tuned for very specific applications.

For our use of the specular highlight, it is important to prevent highlight clipping when capturing it in an image. The shapes of the specular highlights can depend on the surface structure of the illuminated microlens arrays. There will be the brightest highlight in one section of the microlens image and then the highlight will fall off depending on the shape of the lens and the distribution of light from the source. A typical microscope image for the highlight created by cylindrical microlenses illuminated by a 45° incident fiber-optic source is illustrated in FIG. 3. The light source, microlens set-up, and microscope reflected image are shown in FIG. 3.

Color mirrors created by optical interference coatings have the same specular behavior as their bandpass filter counterparts. Their color is not created by a combination of absorption and scatter, as with paint, but by interference of multiple layers of thin films. There are many different interference coating design recipes that can be used when developing a color mirror: some that are all dielectric in nature, others that incorporate metal layers. The spectral reflectance of an interference coating design is based on the interference of reflected light off of each film layer interface for each wavelength of light. An interface is where the refractive index differs between two mediums or film layers. The incident light reflects off of each independent interface and changes phase. Depending on the phase, $\phi$ of each reflected beam, the beams can combine completely due to constructive interference (where the phase difference, $\Delta\phi$, is a multiple of $2\pi$), null each other out completely due to destructive interference ($\Delta\phi$ is an odd multiple of $\pi$), or create an intermediate magnitude between the two. The amount of light reflected and the phase on reflectance is controlled by the thickness of the layer and its refractive index.

The designs used for these color mirror targets are similar to some used for anti-counterfeiting effect pigments. P. Coombs and R. Phillips, "Transparent optically variable device," (1994), patent U.S. Pat. No. 5,278,590; R. W. Phillips, "Optically variable films, pigments, and inks," in SPIE Proceedings, Optical Thin Films III: New Developments, Vol. 1323 (1990) pp. 98-109; R. W. Phillips, M. Nofi, and R. Slusser, "Color effects from thin film designs," in 8th International Conference on Vacuum Web Coating, (Las Vegas, Nev., USA, 1994) pp. 270-284; R. W. Phillips and A. F. Bleikolm, "Optical coatings for document security," Appl. Opt. 35, p. 5529 (1996); P. Coombs and R. Phillips, "Optically variable interference device with peak suppression," (1998), patent EP0 472,371 B1; B. Baloukas, "Thin Film-Based Optically Variable Security Devices: From Passive to Active," Ph.D. thesis, École Polytechnique de Montreal (2012), which is hereby incorporated by reference in its entirety.

A simple principle for reduced angle sensitivity in these designs was used for all of the color mirrors: keep whatever dielectric materials used to a minimum optical thickness for a particular wavelength, shown in Equation 1 where $\lambda$ is the wavelength of light, n is the refractive index of the dielectric film and d is the physical thickness. Large optical thickness and low index of refraction of a dielectric film layer are directly proportional to large angle sensitivity in optical interference coatings.

$$\lambda = nd \quad (1)$$

The invention will be further illustrated with reference to the following specific examples. It is understood that these examples are given by way of illustration and are not meant to limit the disclosure or the claims to follow.

Example 1

Figure 4:
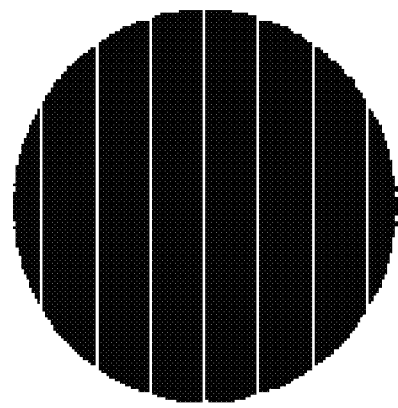
FIG. 4 is an image of the FIG. 3 microscope image following thresholding to identify locations where signals are analyzed.

Sixteen color mirror designs were fabricated on a series of plastic microlens samples. These mirrors were designed to have no more than three film layers to save on production costs but still have reflected spectral shapes that covered different regions in the visible spectrum. Each color mirror was created by depositing either a single layer of titanium dioxide ($TiO_2$) directly on the plastic substrate, a protective layer of silicon dioxide ($SiO_2$) on aluminum (Al), or three layer system of metal-dielectric-metal (opaque Al, $TiO_2$, and a thin, translucent layer of Inconel metal). The protective layer of $SiO_2$ produced reflectance similar to that of a bare metal surface. In both the single layer of $TiO_2$ and the three layer designs, the optical thickness of the $TiO_2$ determines the color reflected. The designed spectral reflectance profiles are shown in FIG. 4 (Theory) and the individual layer physical thicknesses for each sample are listed in Table 1. FIG. 4 also compares the designed color mirrors (Theory) with measurements of the fabricated target samples (Measured) using an off-axis illumination microscope with a liquid crystal tunable filter and monochrome detector, that is, a microspectrophotometer. The similarity of these spectra demonstrates that microlens color mirrors can be effective reference samples for off-axis illumination microscopy.

TABLE 1

Coating Matrix. Film physical thickness in nanometers.

| Part # | Al | SiO$_2$ | TiO$_2$ | Inconel | Color |
|---|---|---|---|---|---|
| 1 | | | 150 | | Blue |
| 2 | | | 170 | | Cyan |
| 3 | | | 225 | | Yellow |
| 4 | | | 280 | | Magenta |
| 5 | 100 | 30 | | | White |
| 6 | 100 | | 70 | 8 | Sky Blue |
| 7 | 100 | | 140 | 8 | Gold |
| 8 | 100 | | 160 | 8 | Magenta |
| 9 | 100 | | 180 | 8 | Violet |
| 10 | 100 | | 200 | 8 | Blue |
| 11 | 100 | | 215 | 8 | Cyan |
| 12 | 100 | | 235 | 8 | Bluish-green |
| 13 | 100 | | 250 | 8 | Yellowish-green |
| 14 | 100 | | 265 | 8 | Yellow |
| 15 | 100 | | 280 | 8 | Light Orange |
| 16 | 100 | | 330 | 8 | Pink |

Example 2

Figure 5:
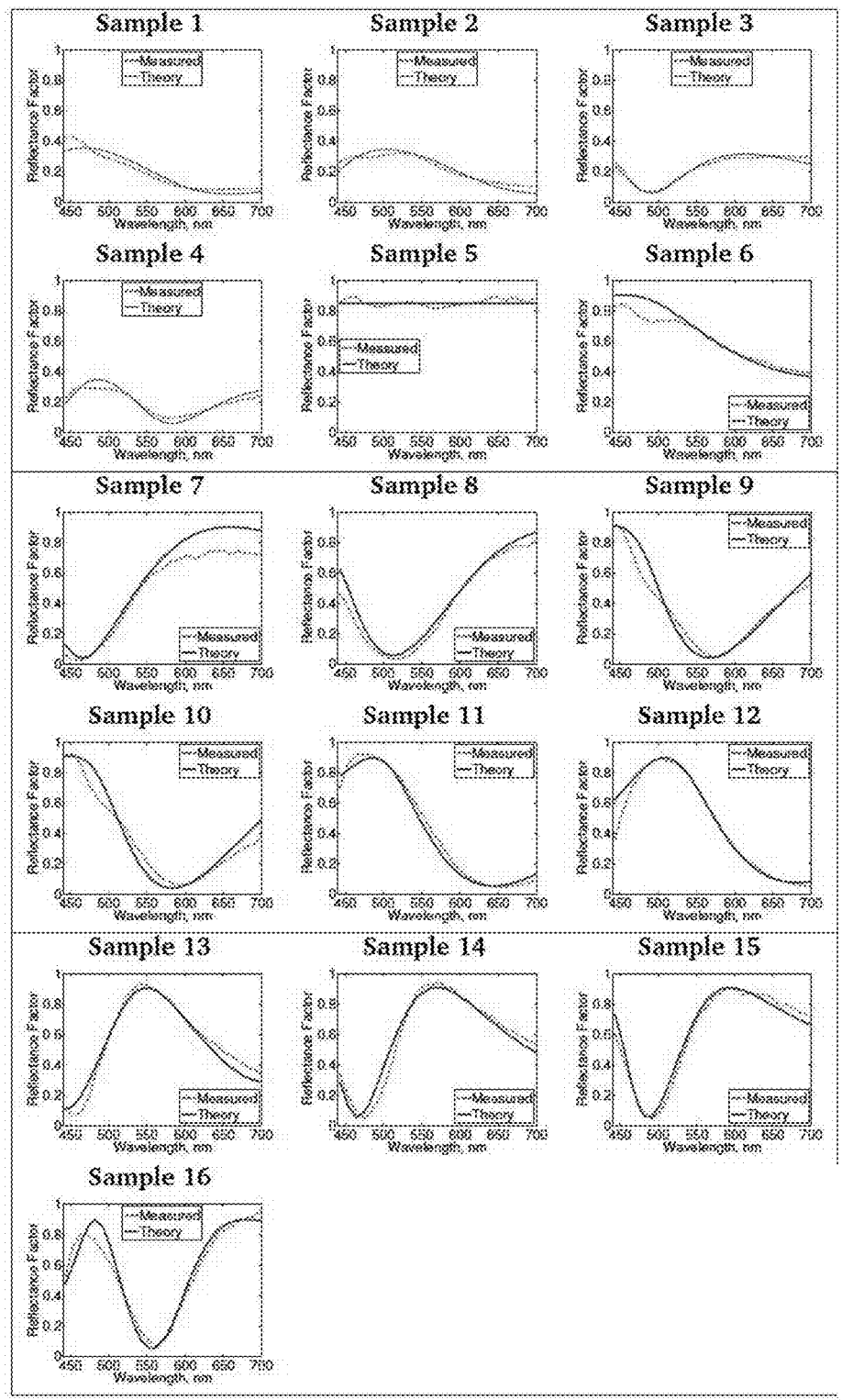
FIG. 5. shows measured spectra from 16 fabricated interference coatings applied to a substrate containing convex microlens targets and measured with a off-axis illumination system microscope and theoretical spectra predicted using multi-layer design software.

The 16 microlens target samples were used to verify the accuracy of an off-axis illumination microscope affixed with a liquid crystal tunable filter and monochrome detector. Eight ceramic tiles were measured using a conventional bidirectional spectrophotometer (Eye-One) and the off-axis illumination microscope affixed with a liquid crystal tunable filter and monochrome detector. The spectra are compared in FIG. 5. The similarity of the spectra for each tile verifies the utility of microlens color mirrors for measurement verification.

Example 3

Multispectral imaging is a technique to estimate spectral reflectance from camera systems with much fewer channels than a true spectral system have dozens to hundreds of channels (known as hyperspectral imaging). One approach to multispectral imaging is using an color camera (RGB) with its infrared blocking filter removed and imaging sequentially with either two color filters with dissimilar spectral transmittance or two lights with dissimilar spectral power distributions (dual-RGB imaging). Using a reference color target with measured spectral reflectance and/or colorimetric coordinates, a linear transformation is derived where camera signals can be transformed to spectral reflectance and/or colorimetric coordinates. This calibrates the imaging system for these two scales. U.S. Pat. No. 7,554,586 to Francisco H. Imai and Roy S. Berns, System and Method for Scene Image Acquisition and Spectral Estimation Using a Wide-band Multi-channel Image Capture, Jun. 30, 2009, Assignee: Rochester Institute of Technology (Rochester, N.Y.), which is hereby incorporated by reference in its entirety.

Figure 6:
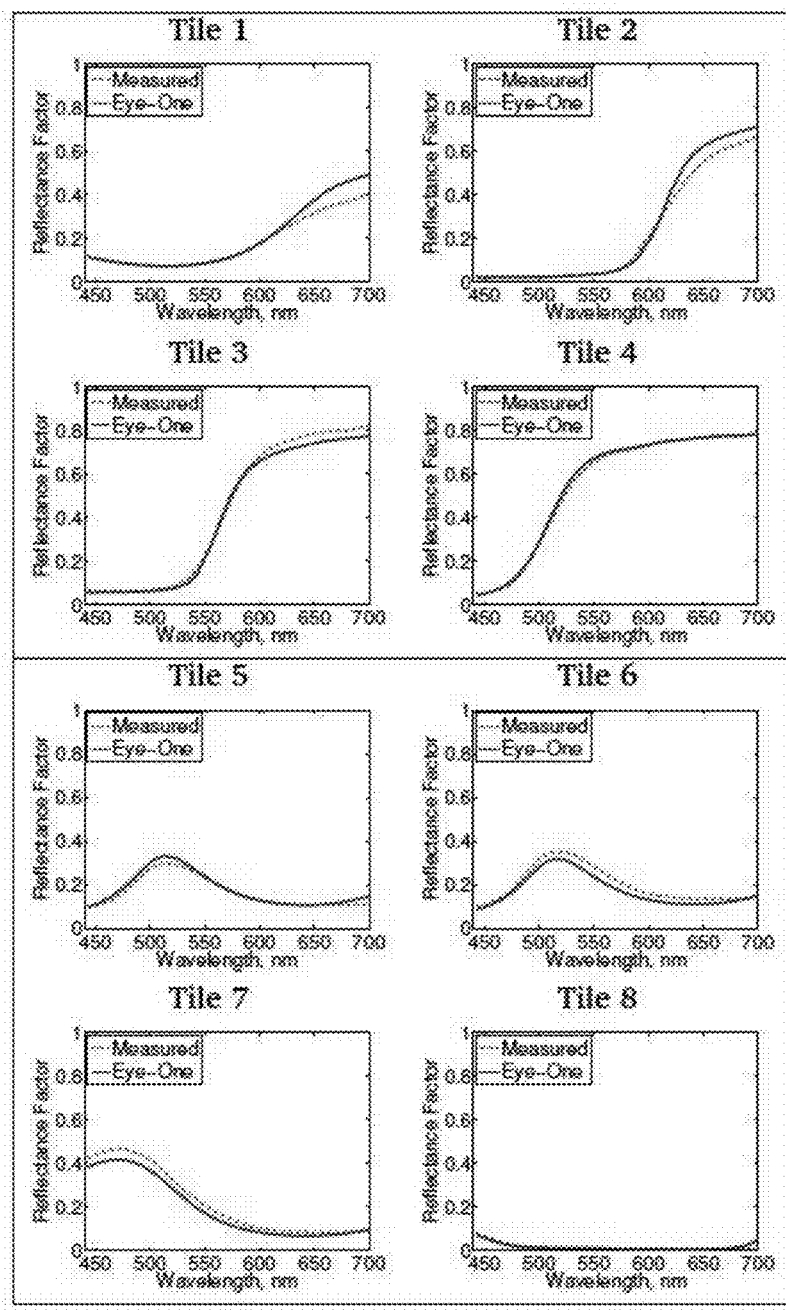
FIG. 6 shows a comparison of eight tile samples measured using a reflection spectrophotometer (Eye-one) and using an off-axis illumination system microscope (Measured)

A camera model was defined to predict signals using a dual-RGB multispectral imaging system attached to an off-axis illumination microscope. The system was a CMOS RGB sensor without its infrared blocking filter and a cyan and a yellow filter. The spectral sensitivities are shown in FIG. 6.

Figure 7:
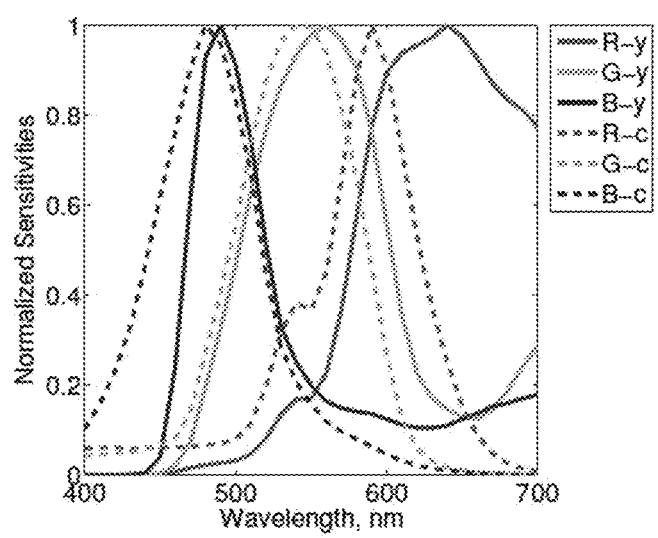
FIG. 7 shows the spectral sensitivities of a computational dual-RGB multispectral off-axis illumination microscope.

A set of mircolens color mirrors were designed to use as a color target, the spectral reflectances plotted in FIG. 7. J. D. T. Kruschwitz and R. S. Berns (2014), Imaging Color Target for Off-Axis Illumination Reflectance Microscopy, Color and Imaging Conference, 2014, pp. 247-252, which is hereby incorporated by reference in its entirety.

Camera signals were calculated the color mirrors imaged using the dual-RGB off-axis illumination microscope. A linear transformation was derived to transform camera signals to spectral reflectance.

Figure 8:
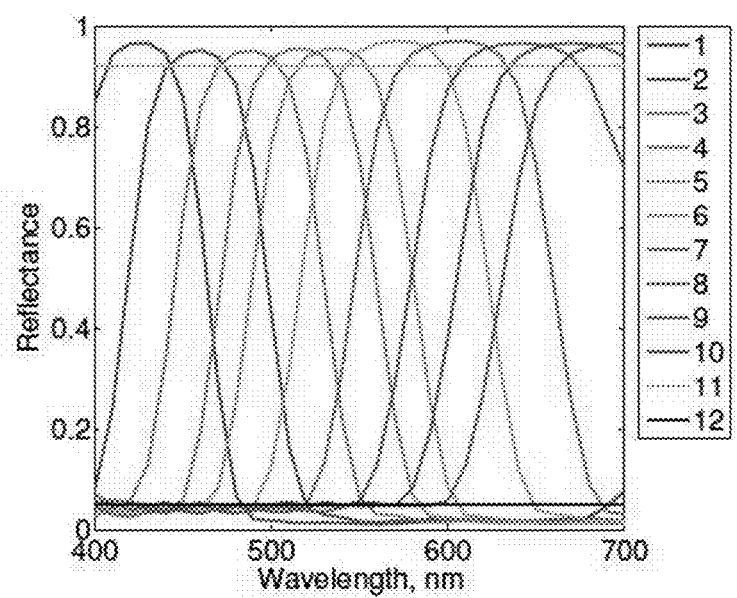
FIG. 8 shows the spectral reflectance of a set of micromirrors designed to calibrate multi-spectral imaging systems.
Figure 9:
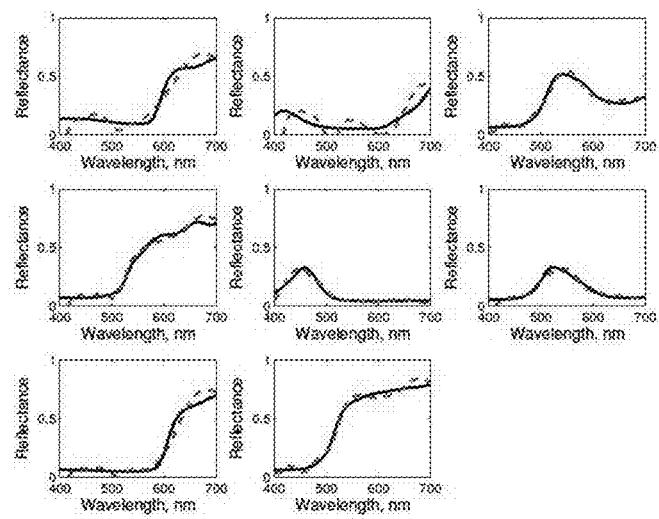
FIG. 9 shows the predicted spectral reflectance of eight painted samples measured using a dual-RGB multispectral off-axis illumination microscope calibrated using the micromirrors plotted in FIG. 8.

Camera signals were calculated for a painted color target (Xrite ColorChecker Classic) measured using the dual-RGB off-axis illumination microscope. Comparisons between spectral reflectance measured using the microscope imaging system (red dashed lines) and a conventional bidirectional spectrophotometer (black lines) are plotted in FIG. 8 for eight representative samples. The similarity of spectra indicates the utility of microlens color mirrors for calibrating an off-axis illumination microscope.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A spectral target for determining the spectral reflectance factor and/or colorimetric coordinates of a sample, comprising:
    a mirror-like substrate containing a plurality of microstructures arranged in an array across the surface of the substrate and each one of the plurality of microstructures having an opaque multi-layer spectrally selective coating with a specific spectral reflectance profile, wherein the substrate has multiple spectral selectivity profiles in multiple locations.

2. The spectral target of claim 1, wherein the microstructure comprises, a microlense, retro-reflector, pyramid, moth-eye, or Fresnel structure.

3. The spectral target of claim 1, wherein the microstructure comprises a plurality of microlenses.

4. The spectral target of claim 1, wherein the spectral selectivity profiles are tuned to specific applications.

5. The spectral target of claim 1, wherein the spectral selectivity profiles encompass different spectral regions.

6. The spectral target of claim 1, wherein the multi-layer coating reflects multiple colors.

7. The spectral target of claim 1, wherein spectral reflectance profile controls reflected on-axis and off axis color.

8. The spectral target of claim 1, wherein the substrate is optically smooth.

9. The spectral target of claim 1, wherein the microstructure controls the direction and pattern of reflected light.

* * * * *